United States Patent [19]
Baran, Jr. et al.

[11] Patent Number: 6,127,430
[45] Date of Patent: Oct. 3, 2000

[54] MICROEMULSIONS CONTAINING WATER AND HYDROFLUROETHERS

[75] Inventors: Jimmie R. Baran, Jr.; Mark J. Pellerite, both of Woodbury, Minn.

[73] Assignee: 3M Innovative Properties Company, St. Paul, Minn.

[21] Appl. No.: 09/212,559

[22] Filed: Dec. 16, 1998

[51] Int. Cl.[7] ..................................................... B01F 17/42
[52] U.S. Cl. ................................ 516/24; 516/26; 516/30; 252/312
[58] Field of Search ................................... 516/30, 24, 26; 252/312

[56] References Cited

U.S. PATENT DOCUMENTS

| | | |
|---|---|---|
| 3,453,333 | 7/1969 | Litt et al. . |
| 3,772,195 | 11/1973 | Francen . |
| 3,778,381 | 12/1973 | Rosano et al. . |
| 3,900,372 | 8/1975 | Childs et al. . |
| 4,090,967 | 5/1978 | Falk . |
| 4,099,574 | 7/1978 | Cooper et al. . |
| 4,242,516 | 12/1980 | Mueller . |
| 4,272,615 | 6/1981 | Yoneyama et al. . |
| 4,359,096 | 11/1982 | Berger . |
| 4,383,929 | 5/1983 | Bertocchio et al. . |
| 4,472,286 | 9/1984 | Falk . |
| 4,536,298 | 8/1985 | Kamei et al. . |
| 4,722,904 | 2/1988 | Feil . |
| 4,795,764 | 1/1989 | Alm et al. . |
| 4,975,468 | 12/1990 | Yiv . |
| 4,983,769 | 1/1991 | Bertocchio et al. . |
| 4,987,154 | 1/1991 | Long, Jr. . |
| 5,085,786 | 2/1992 | Alm et al. . |
| 5,275,669 | 1/1994 | Van Der Puy et al. . |
| 5,558,853 | 9/1996 | Quay . |
| 5,610,128 | 3/1997 | Zyhowski et al. . |
| 5,658,962 | 8/1997 | Moore et al. . |
| 5,667,772 | 9/1997 | Zastrow et al. . |
| 5,750,797 | 5/1998 | Vitcak et al. . |
| 5,762,138 | 6/1998 | Ford et al. ............................... 507/255 |
| 5,856,286 | 1/1999 | Nalewajek et al. ....................... 510/288 |
| 5,911,915 | 6/1999 | Fonsny et al. ........................... 252/312 |

FOREIGN PATENT DOCUMENTS

| | | |
|---|---|---|
| 0 051 526 A1 | 5/1982 | European Pat. Off. . |
| 0 450 855 A2 | 10/1991 | European Pat. Off. . |
| 2 287 432 | 11/1976 | France . |
| 1 294 949 | 5/1969 | Germany . |
| 2-202599 | 8/1990 | Japan . |
| 9-111653 | 4/1997 | Japan . |
| 10-18176 | 1/1998 | Japan . |
| WO 93/11280 | 6/1993 | WIPO . |
| WO 93/11868 | 6/1993 | WIPO . |
| WO 94/19101 | 9/1994 | WIPO . |
| WO 95/31965 | 11/1995 | WIPO . |
| WO 96/22356 | 7/1996 | WIPO . |
| WO 96/40057 | 12/1996 | WIPO . |
| WO 97/33563 | 9/1997 | WIPO . |
| WO 98/59105 | 12/1998 | WIPO . |

OTHER PUBLICATIONS

P. S. Zurer, "Looming Ban on Production of CFCs, Halons Spurs Switch to Substitutes," *Chemical & Engineering News*, pp. 12–18, Nov. 15, 1993.

Yamashita et al., International Conference on CFC and BFC (Halons), Shanghai, China, Aug. 7–10, 1994, pp. 55–58.

*Primary Examiner*—Jacqueline V. Howard
*Attorney, Agent, or Firm*—Scott A. Bardell

[57] ABSTRACT

The invention provides a microemulsion that comprises from 0.1 to 99.0 parts by weight hydrofluoroether, from 1.0 to 99.9 parts by weight water, the sum of the parts of hydrofluoroether and water being 100 parts, and fluorinated surfactant. The microemulsions of the invention preferably contain a mixture of fluorinated surfactants and may also contain a non-fluorinated surfactant. The microemulsions of the invention may also further contain cosurfactant and/or cosolvent.

21 Claims, 4 Drawing Sheets

MICROEMULSIONS CONTAINING WATER AND HYDROFLUROETHERS

BACKGROUND OF THE INVENTION

This invention relates to microemulsions comprising water and hydrofluoroethers.

Emulsions are typically systems that consist of two or more phases of immiscible liquids, such as oil and water. Typically there are two phases contained in an emulsion (although multiple emulsions do exist): a dispersed phase, consisting of one liquid broken into droplets, and a continuous phase, consisting of the other liquid surrounding the droplets of the dispersed phase.

When two immiscible liquids such as a hydrocarbon oil and water are combined, the water will separate to the bottom of the vessel because it has the higher density. If the oil is a fluorocarbon, it will separate to the bottom of the vessel because it is more dense than water. This immiscibility is caused by high interfacial tension between the oil and the water.

In general, emulsion formation requires that an emulsifying agent (a surfactant) and energy be added to the system. This energy can be in the form of mechanical agitation, ultrasound, and/or heat. The surfactant acts to reduce the interfacial tension between the two phases; this allows an increase in the interfacial area, and increases the number of droplets of dispersed phase in a volume of the continuous phase.

For some applications it is desirable that these droplets be finely and uniformly distributed throughout the continuous phase. This can be accomplished through formation of microemulsions, which generally have particle sizes less than 100 nm. This small particle size provides a homogeneous, transparent or nearly transparent mixture that appears to be a solution. However, a dispersed phase having such a small particle size typically requires relatively more surfactant than an analogous emulsion in order to produce the necessary reduction in interfacial tension and increase in interfacial area.

Microemulsions and emulsions (or macroemulsions) differ in several ways. Typically, microemulsions form spontaneously under appropriate conditions and are thermodynamically stable. Furthermore, any phase separation resulting from freezing or a change in storage temperature is reversible, in that the microemulsion will reform when the original storage conditions are restored with perhaps some minimal agitation. Conversely, emulsions typically require additional energy to form, and will increase in particle size with time until the two immiscible components separate to their more thermodynamically preferred state.

Microemulsions may be oil- or water-continuous or may be bicontinuous. An oil-continuous system consists of water dispersed in oil, while a water-continuous system consists of oil dispersed in water. A bicontinuous system has no single dispersed phase and is typically considered to be a series of intertwining networks of the two phases.

Microemulsions generally maintain the viscosity of their continuous phase. In certain regions of the phase diagram, more complex micellar and other structures occur that lead to gels or highly viscous systems. Such systems can be similar to the bicontinuous structure mentioned above, or liquid crystalline gels, bilayered systems, rodlike or wormlike micelles, and others. In certain regions of phase space microemulsions can exist in equilibrium with other phases such as liquid crystalline phases.

Typically, systems that contain a fluorinated oil require relatively large amounts of a fluorinated surfactant in order to produce a microemulsion because such fluorinated surfactants are not very efficient at emulsification. This generally leads to a smaller one-phase region in the phase diagram wherein the microemulsion will form.

SUMMARY OF THE INVENTION

The invention provides a microemulsion that comprises from 0.1 to 99.0 parts by weight hydrofluoroether, from 1.0 to 99.9 parts by weight water, the sum of the parts of hydrofluoroether and water being 100 parts, and fluorinated surfactant. The microemulsions of the invention preferably contain a mixture of fluorinated surfactants and may also contain a non-fluorinated surfactant. The microemulsions of the invention may also further contain cosurfactant(s) and/or cosolvent(s).

Microemulsions of the invention may be formulated and prepared so to form at temperatures that range from about −10° C. to the boiling point of the HFEs used, or water in the microemulsion, whichever is lower. A preferred temperature range for the formation of microemulsions of the invention is from 0° C. to the lower of the boiling point of HFEs used or water in the microemulsion, with a range of 10° C. to 40° C. being more preferred, and ambient temperature being even more preferred.

The microemulsions of the invention are useful in applications such as cleaning agents, solvents, and delivery systems.

Advantageously, the microemulsions of the invention are transparent or nearly transparent due to the small particle size of the dispersed phase and they are easy to form, thus minimal processing is required for their preparation.

DETAILED DESCRIPTION OF THE INVENTION

Hydrofluoroethers

Figure 1:
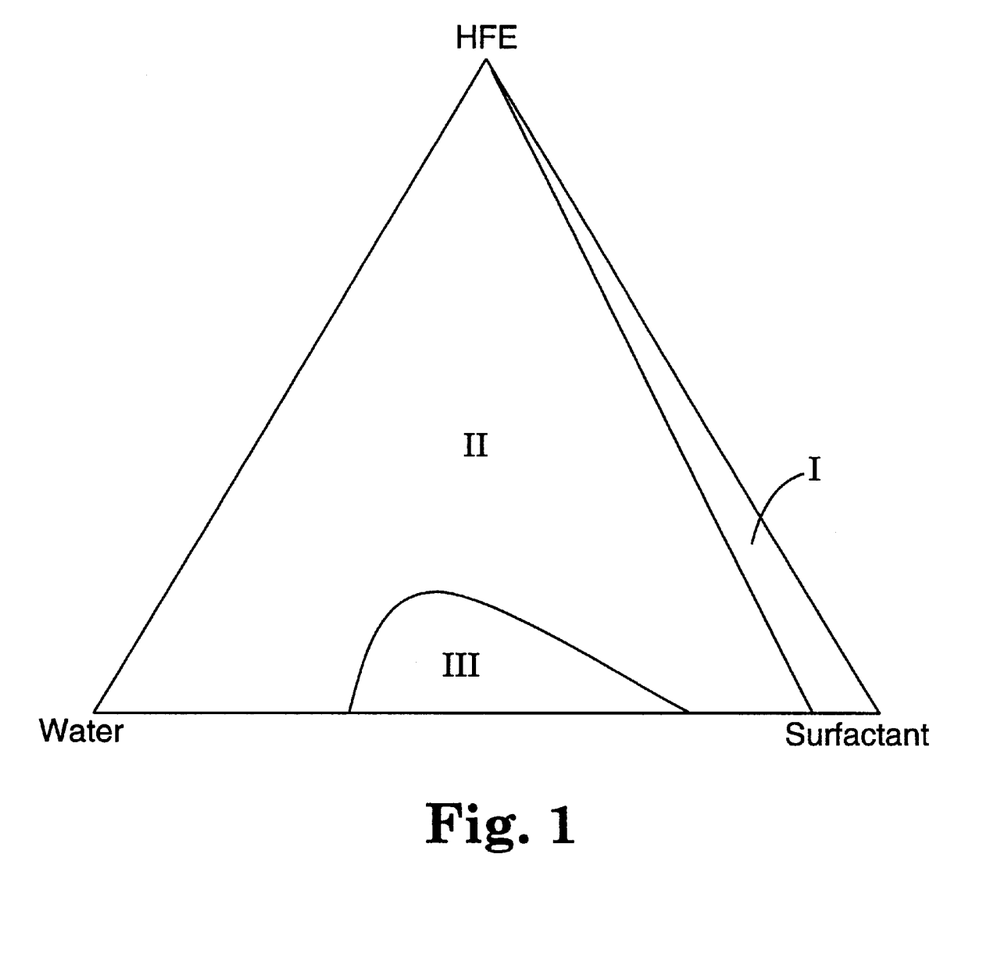
FIG. 1 shows a phase diagram for the water/perflurobutyl methyl ether/fluorinated alkyl alkoxylate (FLUORAD™ FC- 171, available from Minnesota Mining and Manufacturing Company, St Paul, Minn.) system at room temperature (23° C.). Region I is a single-phase region, Region II is a two-phase region and Region III is a liquid crystal region.
Figure 2:
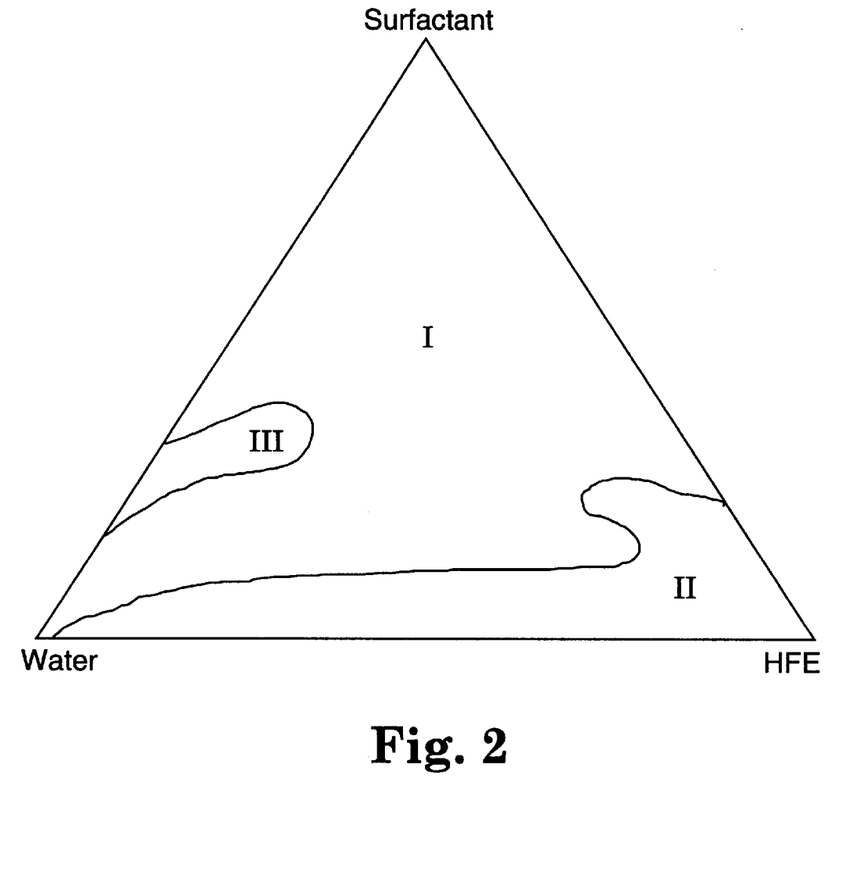
FIG. 2 shows a phase diagram for the water/ perflurobutyl ethyl ether/ fluorinated alkyl alkoxylate (FLUORAD™ FC-171) system at 10° C. In this case the surfactant system consisted of a mixture of fluorinated alkyl alkoxylate (39.4%),tetrabutylammonium perfluorooctanoate (39.4%), and isopropanol (21.2%). Region I is a single-phase region, Region II is a two-phase region, and Region III is a liquid crystal region.
Figure 3:
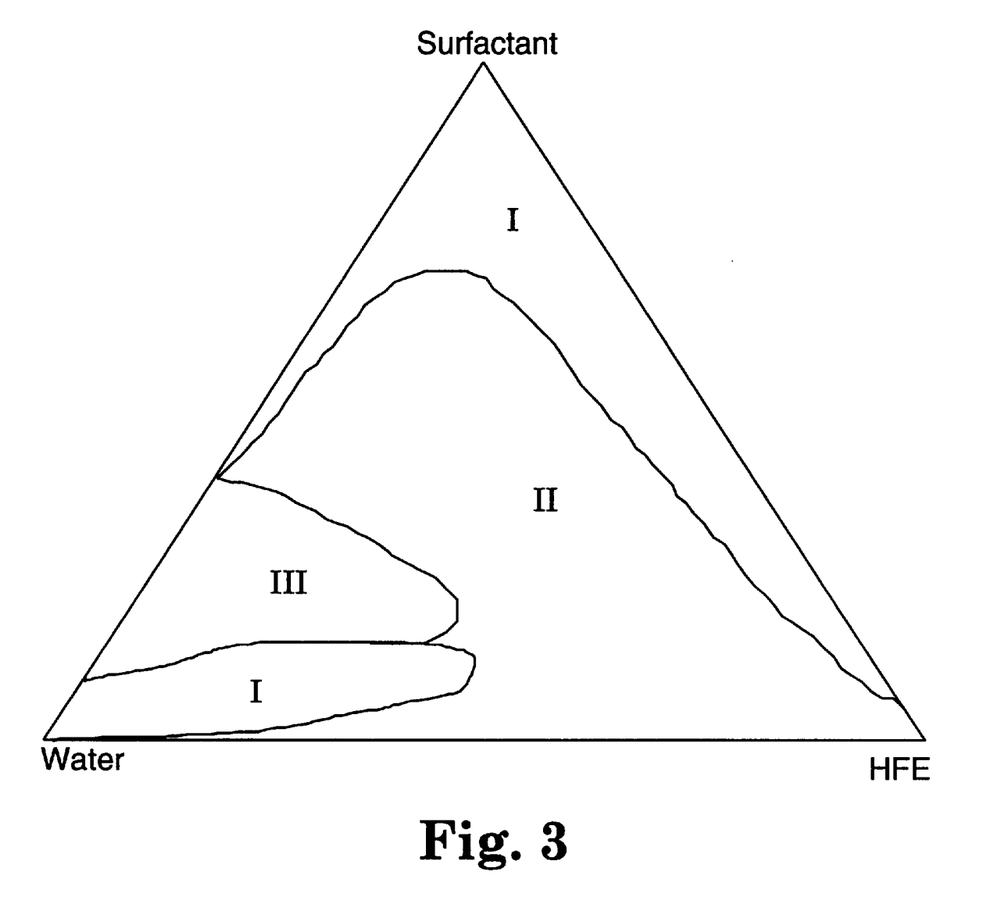
FIG. 3 shows a phase diagram for the system of FIG. 2 at 25° C. Region I is a single-phase region, Region II is a two-phase region, and Region III is a liquid crystal region.
Figure 4:
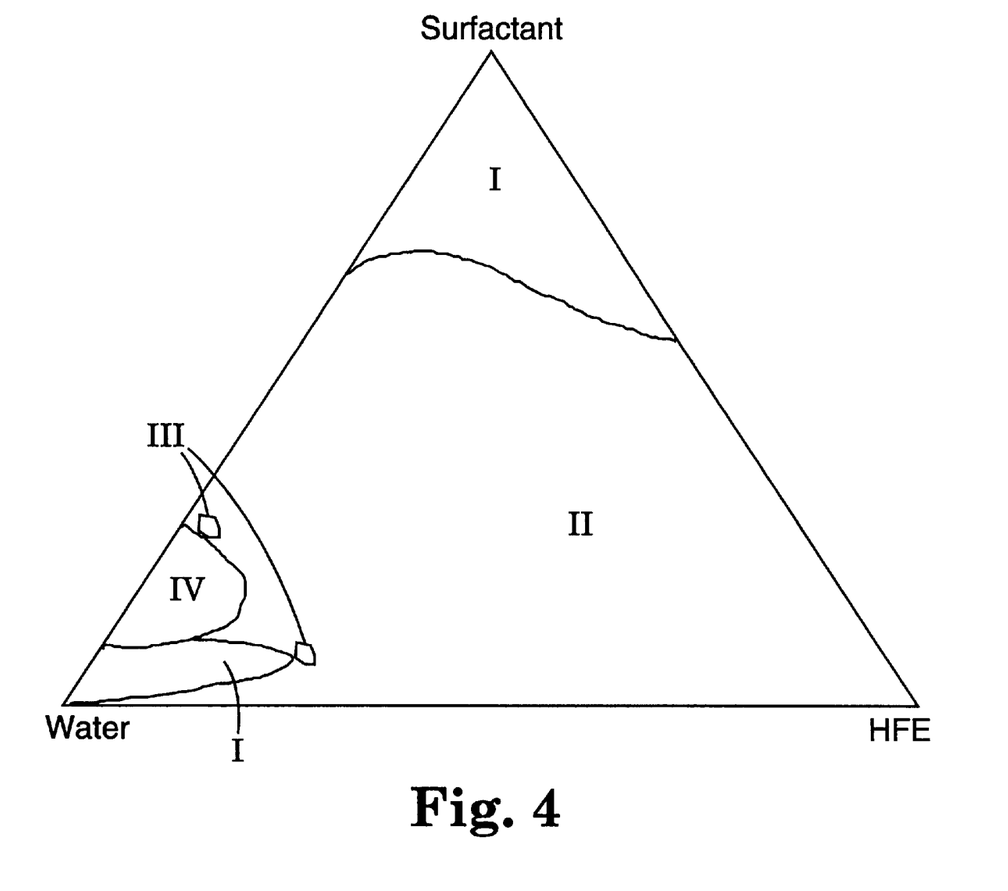
FIG. 4 shows a phase diagram for the system of FIG. 2 at 40° C. Region I is a single-phase region, Region II is a two-phase region, Region III is a three-phase region, and Region IV is a liquid crystal region.

Hydrofluoroethers (HFEs) suitable for use in the process are generally low polarity chemical compounds minimally containing carbon, fluorine, hydrogen, and catenary (that is, in-chain) oxygen atoms. HFEs can optionally contain additional catenary heteroatoms, such as nitrogen and sulfur.

HFEs have molecular structures which can be linear, branched, or cyclic, or a combination thereof (such as alkylcycloaliphatic), and are preferably free of ethylenic unsaturation, having a total of about 4 to about 20 carbon atoms. Such HFEs are known and are readily available, either as essentially pure compounds or as mixtures.

Preferred hydrofluoroethers can have a boiling point in the range from about 30° C. to about 275° C., preferably from about 50° C. to about 200° C., even more preferably from about 50° C. to about 110° C.

It is very desirable that the hydrofluoroether be non-flammable. To be non-flammable, the relationship between the fluorine, hydrogen and carbon atoms of the HFE should meet the requirements of Equation I.

Equation I

\# of F atoms/(\# H atoms+\# C—C bonds)$\geq 0.8$

For example, the calculation for $C_4F_9OCH_3$ is $9/(3+3)=1.5$. Therefore, this compound is nonflammable and clearly is very useful in this invention. In contrast, the calculation for $C_3F_7C_3H_7$, is $7/(7+4)=0.64$, meaning that $C_3F_7OC_3H_7$ is flammable and not particularly useful in this invention. In general, increasing the number of fluorine atoms, decreasing the number of hydrogen atoms, or decreasing the number of carbon-carbon bonds each increases the flash point of the HFE.

Useful hydrofluoroethers include two varieties: segregated hydrofluoroethers and omega-hydrofluoroalkylethers. Structurally, the segregated hydrofluoroethers comprise at least one mono-, di-, or trialkoxy-substituted perfluoroalkane, perfluorocycloalkane, perfluorocycloalkyl-containing perfluoroalkane, or perfluorocycloalkylene-containing perfluoroalkane compound.

Such HFEs are described in WO 96/22356 and are represented below in Formula I:

$R_f$—(O—$R_h$)$_x$ (Formula I)

wherein:

x is from 1 to about 3;

when x is 1, $R_f$ is selected from the group consisting of linear or branched perfluoroalkyl groups having from 2 to about 15 carbons, perfluorocycloalkyl groups having from 3 to about 12 carbon atoms, and perfluorocycloalkyl-containing perfluoroalkyl groups having from 5 to about 15 carbon atoms;

when x is 2, $R_f$ is selected from the group consisting of linear or branched perfluoroalkanedlyl groups or perfluoroalkylidene groups having from 2 to about 15 carbon atoms, perfluorocycloalkyl- or perfluorocycloalkylene-containing perfluoroalkanediyl or perfluoroalkylidene groups having from 6 to about 15 carbon atoms, and perfluorocycloalkylidene groups having from 3 to about 12 carbon atoms;

when x is 3, $R_f$ is selected from the group consisting of linear or branched perfluoroalkanetriyl groups or perfluoroalkylidene groups having from 2 to about 15 carbon atoms, perfluorocycloalkyl- or perfluorocycloalkylene-containing perfluoroalkanetriyl or perfluoroalkylidene groups, having from 6 to about 15 carbon atoms, and perfluorocycloalkanetriyl groups having from 3 to about 12 carbon atoms;

in all cases, $R_f$ can be optionally terminated with an $F_5S$-group;

each $R_h$ is independently selected from the group consisting of linear or branched alkyl groups having from 1 to about 8 carbon atoms, cycloalkyl-containing alkyl groups having from 4 to about 8 carbon atoms, and cycloalkyl groups having from 3 to about 8 carbon atoms;

wherein either or both of the groups $R_f$ and $R_h$ can optionally contain one or more catenary heteroatoms; and wherein the sum of the number of carbon atoms in the $R_f$ group and the number of carbon atoms in the $R_h$ group(s) is greater or equal to 4; and wherein the perfluorocycloalkyl and perfluorocycloalkylene groups contained within the perfluoroalkyl, perfluoroalkanediyl, perfluoroalkylidene and perfluoroalkanetriyl groups can optionally and independently be substituted with, for example, one or more perfluoroalkyl groups having from 1 to about 4 carbon atoms.

Preferably, x is 1; $R_f$ is defined as above; $R_h$ is an alkyl group having from 1 to about 6 carbon atoms; $R_f$ but not $R_h$ can contain one or more catenary heteroatoms; and the sum of the number of carbon atoms in $R_f$ and the number of carbon atoms in $R_h$ is greater than or equal to 4. Even more preferably, x is 1; $R_f$ is selected from the group consisting of linear or branched perfluoroalkyl groups having from 3 to about 8 carbon atoms, perfluorocycloalkyl-containing perfluoroalkyl or perfluoroalkylidene groups having from 5 to about 8 carbon atoms, and perfluorocycloalkyl groups having from 5 to about 6 carbon atoms; $R_h$ is an alkyl group having from 1 to about 3 carbon atoms; and $R_f$ but not $R_h$ can contain one or more catenary heteroatoms. The perfluoroalkyl and perfluorocycloalkylene groups contained within the perfluoroalkyl, perfluoroalkanediyl, perfluoroalkylidene, and perfluoroalkanetriyl groups can optionally and independently be substituted with, for example, one or more perfluoromethyl groups.

Representative hydrofluoroether compounds described by Formula I include the following:

-continued

C$_2$F$_5$NCF$_2$CF$_2$CF$_2$OC$_2$H$_5$
  |
  CF$_3$ (C$_3$F$_7$)$_2$NCF$_2$CF$_2$CF$_2$OCH$_3$

(C$_3$F$_7$)$_2$NCF$_2$CF$_2$CF$_2$OC$_2$H$_5$     (C$_3$F$_7$)$_2$NCF$_2$CF$_2$CF$_2$OC$_3$H$_7$ $n = 1\text{-}4$ $n = 1\text{-}4$

$n = 1\text{-}4$

$n = 1\text{-}4$

$n = 1\text{-}4$

(C$_4$F$_9$)$_2$N(CF$_2$)$_3$OCH$_3$     (C$_2$F$_5$)$_2$N(CF$_2$)$_6$OCH$_3$

-continued

C$_3$F$_7$CF(OC$_2$H$_5$)CF(CF$_3$)$_2$
C$_2$F$_5$CF(OC$_2$H$_5$)CF(CF$_3$)$_2$
C$_2$F$_5$CF(OCH$_3$)CF(CF$_3$)$_2$
CF$_3$CF(OCH$_3$)CF(CF$_3$)$_2$ wherein cyclic structures designated with an interior "F" are perfluorinated.

Preferred segregated hydrofluoroethers include n-C$_3$F$_7$OCH$_3$, (CF$_3$)$_2$CFOCH$_3$, n-C$_4$F$_9$ OCH$_3$, (CF$_3$)$_2$CFCF$_2$OCH$_3$, n-C$_4$F$_9$OC$_2$H$_5$, (CF$_3$)$_2$CFCF$_2$OC$_2$H$_5$, (CF$_3$)$_3$COCH$_3$, CH$_3$O(CF$_2$)$_4$OCH$_3$, and CH$_3$O(CF$_2$)$_6$OCH$_3$.

Segregated hydrofluoroethers (that is, HFEs described generally by Formula I) can be prepared by alkylation of perfluorinated alkoxides prepared by the reaction of the corresponding perfluorinated acyl fluoride or perfluorinated ketone with an anhydrous alkali metal fluoride (for example, potassium fluoride or cesium fluoride) or anhydrous silver fluoride in an anhydrous polar aprotic solvent. (See, for example, the preparative methods described in French Patent Publication No. 2,287,432 and German Patent Publication No. 1,294,949, supra). Alternatively, a fluorinated tertiary alcohol can be allowed to react with a base (for example, potassium hydroxide or sodium hydroxide) to produce a perfluorinated tertiary alkoxide which can then be alkylated by reaction with alkylating agent, such as described in U.S. Pat. No. 5,750,797, which is herein incorporated by reference.

Suitable alkylating agents for use in the preparation of segregated hydrofluoroethers include dialkyl sulfates (for example, dimethyl sulfate), alkyl halides (for example, methyl iodide), alkyl p-toluene sulfonates (for example, methyl p-toluenesulfonate), alkyl perfluoroalkanesulfonates (for example, methyl perfluoromethanesulfonate), and the like. Suitable polar aprotic solvents include acyclic ethers such as diethyl ether, ethylene glycol dimethyl ether, and diethylene glycol dimethyl ether; carboxylic acid esters such as methyl formate, ethyl formate, methyl acetate, diethyl carbonate, propylene carbonate, and ethylene carbonate; alkyl nitrites such as acetonitrile; alkyl amides such as N,N-dimethylformamide, N,N-diethylformamide, and N-methylpyrrolidone; alkyl sulfoxides such as dimethyl sulfoxide; alkyl sulfones such as dimethylsulfone, tetramethylene sulfone, and other sulfolanes; oxazolidones such as N-methyl-2-oxazolidone; and mixtures thereof.

Suitable perfluorinated acyl fluorides can be prepared by electrochemical fluorination (ECF) of the corresponding hydrocarbon carboxylic acid (or a derivative thereof), using either anhydrous hydrogen fluoride (Simons ECF) or KF$_2$·HF (Phillips ECF) as the electrolyte. Perfluorinated acyl fluorides and perfluorinated ketones can also be prepared by dissociation of perfluorinated carboxylic acid esters (which can be prepared from the corresponding hydrocarbon or partially-fluorinated carboxylic acid esters by direct fluorination with fluorine gas). Dissociation can be achieved by contacting the perfluorinated ester with a source of fluoride ion under reacting conditions (see the method described in U.S. Pat. No. 3,900,372 (Childs), the description of which is incorporated herein by reference) or by combining the ester with at least one initiating reagent selected from the group consisting of gaseous, nonhydroxylic nucleophiles; liquid, non-hydroxylic nucleophiles; and mixtures of at least one non-hydroxylic nucleophile (gaseous, liquid, or solid) and at least one solvent which is inert to acylating agents.

Initiating reagents which can be employed in the dissociation are those gaseous or liquid, non-hydroxylic nucleophiles and mixtures of gaseous, liquid, or solid, nonhydroxylic nucleophile(s) and solvent (hereinafter termed "solvent mixtures") which are capable of nucleophilic reaction with perfluorinated esters. The presence of small amounts of hydroxylic nucleophiles can be tolerated. Suitable gaseous or liquid, nonhydroxylic nucleophiles include dialkylamines, trialkylamines, carboxamides, alkyl sulfoxides, amine oxides, oxazolidones, pyridines, and the like, and mixtures thereof. Suitable non-hydroxylic nucleophiles for use in solvent mixtures include such gaseous or liquid, non-hydroxylic nucleophiles, as well as solid, non-hydroxylic nucleophiles, for example, fluoride, cyanide, cyanate, iodide, chloride, bromide, acetate, mercaptide, alkoxide, thiocyanate, azide, trimethylsilyl difluoride, bisulfite, and bifluoride anions, which can be used in the form of alkali metal, ammonium, alkyl-substituted ammonium (mono-, di-, tri-, or tetra-substituted), or quaternary phosphonium salts, and mixtures thereof. Such salts are in general commercially available but, if desired, can be prepared by known methods, for example, those described by M. C. Sneed and R. C. Brasted in *Comprehensive Inorganic Chemistry*, Volume Six (The Alkali Metals), pages 61–64, D. Van Nostrand Company, Inc., New York (1957), and by H. Kobler et al. in Justus Liebigs Ann. Chem. 1978, 1937. 1,4-diazabicyclo[2.2.2]octane and the like are also suitable solid nucleophiles.

Other useful hydrofluoroethers are the omega-hydrofluoroalkyl ethers described in U.S. Pat. No. 5,658,962 (Moore et al.), herein incorporated by reference, which can be described by the general structure shown in Formula II:

$$X-R_f'-(O-R_f'')_y-O-R''-H \quad \text{(Formula II)}$$

wherein:

X is either F or H;

$R_f'$ is a divalent perfluorinated organic radical having from 1 to about 12 carbon atoms;

$R_{f''}$ is a divalent perfluorinated organic radical having from 1 to about 6 carbon atoms;

R" is a divalent organic radical having from 1 to 6 carbon atoms, and preferably, R" is perfluorinated; and y is an integer from 0 to 4; with the proviso that when X is F and y is 0, R" contains at least one F atom.

Representative compounds described by Formula II which are suitable for use in the processes of the invention include the following compounds:

$C_4F_9OC_2F_4H$
$HC_3F_6OC_3F_6H$
$HC_3F_6OCH_3$
$C_5F_{11}OC_2F_4H$
$C_6F_{13}OCF_2H$
$C_6F_{13}OC_2F_4OC_2F_4H$
c-$C_6F_{11}CF_2OCF_2H$
$C_3F_7OCH_2F$
$HCF_2O(C_2F_4O)_n(CF_2O)_mCF_2H$, wherein m=0 to 2 and n=0 to 3
$C_3F_7O[C(CF_3)CF_2O]_pCFHCF_3$, wherein p=0 to 5

$C_4F_9OCF_2C(CF_3)_2CF_2H$
$HCF_2CF_2OCF_2C(CF_3)_2CF_2OC_2F_4H$
$C_7F_{15}OCFHCF_3$
$C_8F_{17}OCF_2O(CF_2)_5H$
$C_8F_{17}OC_2F_4OC_2F_4OC_2F_4OCF_2H$

The omega-hydrofluoroalkyl ethers described by Formula II can be prepared by decarboxylation of the corresponding precursor fluoroalkyl ether carboxylic acids and salts thereof or, preferably, the saponifiable alkyl esters thereof, as described in U.S. Pat. No. 5,658,962, which is herein incorporated by reference.

Alternatively, the omega-hydrofluoroalkyl ethers can be prepared by reduction of the corresponding omega-chlorofluoroalkyl ethers (for example, those omega-chlorofluoroalkyl ethers described in WO 93/11868 published application), which is also described in U.S. Pat. No. 5,658,962.

The oil phase of the microemulsions of the invention may also optionally contain HFE compatible solvents, such as other fluorocarbon compounds. Examples of other fluorocarbon compounds which may be used with HFEs to form a microemulsion include perfluorodecalin, perfluoroalkanes such as FLUORINERT™ FC-72 (perfluorohexane, commercially available from Minnesota Mining and Manufacturing Co, St. Paul, Minn.), perfluorotrialkylamines such as FLUORINERT™ FC-40 (perfluorotributylamine, commercially available from Minnesota Mining and Manufacturing Company), perfluoroethers such as FLUORINERT™ FC-75 (perfluoropropyltetrahydrofuran, commercially available from Minnesota Mining and Manufacturing Company), perfluoroalkyl bromides, perfluoroalkyl chlorides, perfluoroalkyl iodides, and hydrofluoroalkanes such as those having the tradename VERTREL, commercially available from E.I. DuPont de Nemours and Co., Wilmington, Del.; and the tradename ZEORORAF, commercially available from Nippon Zeon Co., Ltd., Tokyo, Japan.

Surfactants a) Fluorinated

The microemulsions of the invention can utilize many types of linear or branched surfactants, provided that the primary surfactant is fluorinated. "Primary surfactant" means that the fluorinated surfactant is present in the composition at a level of 50 percent or more by weight of the total amount of surfactant present in the composition.

Suitable fluorochemical or fluorinated surfactants are those having structures as depicted by Formula III:

$$(R_f)_n(Q)_m(Z)_p \quad \text{(Formula III)}$$

and contain one or more fluorinated aliphatic radicals ($R_f$) and one or more polar hydrophilic groups (Z), which radicals and hydrophilic groups are usually connected together by a suitable linking group (Q).

The fluorinated aliphatic radical, $R_f$, can generally be a fluorinated, saturated or unsaturated, monovalent, non-aromatic radical preferably having at least 3 carbon atoms. The aliphatic chain may be linear, branched, or, if sufficiently large, cyclic, and may include catenary oxygen, trivalent nitrogen, or hexavalent sulfur atoms. A fully fluorinated $R_f$ radical is preferred, but hydrogen or chlorine may be present as substituents provided that not more than one atom of either is present for every two carbon atoms, and, preferably, the radical contains at least a terminal perfluoromethyl group. Radicals containing no more than about 20 carbon atoms are preferred because larger radicals usually represent a less efficient utilization of fluorine. Fluoroaliphatic radicals containing about 4 to 12 carbon atoms are more preferred.

The polar hydrophilic group, Z, can be nonionic, ionic (that is, anionic, cationic, or amphoteric), or a combination thereof. Typical nonionic moieties include polyoxyethylene and polyoxypropylene moieties. Typical anionic moieties include carboxylate, sulfonate, sulfate, ether sulfate, or phosphate moieties. Typical cationic moieties include quaternary ammonium, protonated ammonium, sulfonium, and phosphonium moieties. Typical amphoteric moieties include betaine, sulfobetaine, aminocarboxyl, amine oxide, and various other combinations of anionic and cationic moieties. Preferably, Z is a polyoxyalkylene moiety.

The linking group, Q, can be a multivalent, preferably divalent, linking group such as alkylene, arylene, sulfonamidoalkylene, carboxamidoalkylene, alkylenesulfonamidoalkylene, alkyleneoxyalkylene, or alkylenethioalkylene. Alternatively, Q may be absent, in which case $R_f$ and Z are directly connected by a covalent bond.

A particularly useful class of fluoroaliphatic surfactants useful in this invention are those wherein $R_f$, Q, and Z are as defined, and n is 1 or 2, m is 0 to 2, and p is 1 or 2. Representative fluorochemical surfactants according to this formula include the following:

$C_7F_{15}CO_2^-NH_4^+$
$C_8F_{17}SO_3^-K^+$
$C_{10}F_{21}SO_3^-K^+$
$C_8F_{17}C_2H_4SO_3^-K^+$
$C_{12}F_{23}OC_6H_4SO_3^-Na^+$
$C_8F_{17}SO_2N(C_2H_5)CH_2COO^-K^+$
$C_8F_{17}C_2H_4SC_2H_4N^+(CH_3)_2CH_2COO^-$
$C_8F_{17}C_2H_4SC_2H_4COO^-Li^+$
$C^3F_7O(C_3F_6O)_3CF(CF_3)CH_2CH(OH)CH_2N(CH_3)CH_2COO^{-K+}$
$C_8F_{17}SO_2N(C_2H_5)C_2H_4OSO_3^-Na^+$
$C_8F_{17}SO_2N(C_2H_5)C_2H_4OP(O)(O^-NH_4^+)_2$
$C_4F_9SO_2N(H)C_3H_6N^+(CH_3)_2O^-$
$C_8F_{17}SO_2N(H)C_3H_6N^+(CH_3)_2O^-$
$C_{10}F_{21}SO_2N(H)C_3H_6N^+(CH_3)_2O^-$
$C_7F_{15}CF(CF_3)SO_2N(H)C_3H_6N^+(CH_3)_2O^+$
$C_7F_{15}CON(H)C_3H_6N^+(CH_3)_2O^-$ $C_6F_{13}C_2H_4SO_2N(H)C_3H_6N^+(CH_3)_2O^-$
$C_6F_{13}SO_2N(C_2H_4COO^-)^C{}_3H_6N^+(CH_3)_2H$
$C_8F_{17}C_2H_4CONHC_3H_6N^+(CH_3)_2C_2H_4COO^-$
$C_6F_{13}SO_2N(C_3H_6SO_3^-)^C{}_3H_6N^+(CH_3)_2C_2H_4OH$
$C_6F_{13}SO_2N(CH_2CHOHCH_2SO_3{}^3)C_3H_6N^+(CH_3)_2C_2H_4OH$
$C_7F_{15}CF=CHCH_2N(CH_3)CH_2CH_2OSO_3^-Na^+$
$C_8F_{17}SO_2N(H)C_3H_6N^+(CH_3)_3\ Cl^-$
$C_8F_{17}SO_2N(H)C_3H_6N^+(CH_3)_3I^-$
$C_6F_{13}SO_2N(H)C_3H_6N^+(CH_3)_3Cl^-$
$C_6F_{13}SO_2N(C_2H_5)C_3H_6N(H)CH_2CH(OH)CH_2SO_3{}^{-Na+}$
$C_6F_{13}C_2H_4SO_2N(CH_3)C_2H_4N^+(CH_3)_2CH_4COO^-$
$C_6F_{13}C_2H_4SO_2N(C_3H_6N^+(CH_3)_2C_2H_4COO^-$
$C_6F_{13}CH_2CH(OCOCH_3)CH_2N^+(CH_3)_2CH_2COO^-$
$C_8F_{17}SO_2N(C_2H_5)(C_2H_4O)_7CH_3$
$C_8F_{17}SO_2N(C_2H_5)(C_2H_4O)_{14}H$
$C_8F_{17}(C_2H_4O)_{10}H$

Examples of these and other fluorochemical surfactants are described, for example, in U.S. Pat. Nos. 3,772,195 (Francen), 4,090,967 (Falk), 4,099,574 (Cooper et al.), 4,242,516 (Mueller), 4,359,096 (Berger), 4,383,929 (Bertocchio et al.), 4,472,286 (Falk), 4,536,298 (Kamei et al.), 4,795,764 (Alm et al.), 4,983,769 (Bertocchio et al.) and 5,085,786 (Alm et al.). Many of these fluorochemical surfactants are commercially available from Minnesota Mining and Manufacturing Company, having the tradename FLUORAD, or commercially available from E.I DuPont de Nemours and Co., having the tradename ZONYL.

b) Non-Fluorinated

Suitable hydrogenated or non-fluorinated surfactants have structures depicted by Formula IV:

$$(R)_n(Q')_M(Z')_p \qquad \text{(Formula IV)}$$

and contain one or more non-fluorinated radicals (R) and one or more polar hydrophilic groups (Z'), which radicals and hydrophilic groups are usually connected together by a suitable linking group (Q'). The non-fluorinated radical (R) may be a hydrocarbon group $(R_h)$.

The hydrocarbon group, $R_h$, can generally be an aliphatic, aromatic, or mixed aliphatic/aromatic (that is, aralkyl or alkaryl) preferably having at least 8 carbon atoms. The aliphatic portion may be saturated or unsaturated, linear, branched, or, if sufficiently large, cyclic. Either the aliphatic or aromatic portion may include heteroatoms such as chlorine and/or catenary heteroatoms, such as oxygen, nitrogen, or sulfur.

The polar hydrophilic group, Z', can be as described for Z in Formula III.

The linking group, Q', can be a multivalent, preferably divalent, linking group such as carboxamidoalkylene, sulfonamidoalkylene, alkyleneoxyalkylene, or alkylenethioalkylene. Alternatively, Q' may be absent, in which case R and Z are directly connected by a covalent bond Preferred non-fluorinated surfactants include (1) hydrocarbon surfactants having a hydrophilic/lipophilic balance (HLB) from less than 1 to about 70 (dependent upon temperature, HFE structure, presence of cosolvent, and whether water or HFE is the continuous phase); and (2) ionic hydrocarbon surfactants having a carbon chain length from about 8 to about 24 carbon atoms.

Examples of suitable nonionic non-fluorinated surfactants include ethylene oxide-based surfactants such as $C_nH_{2n+1}O(C_2H_4O)_mH$ where n is an integer between about 8 and 18 and m is greater than or equal to about 4; ethoxylated alkylphenols such as where p is an integer between about 4 and about 12 and z is greater than or equal to about 4, having the tradename TRITON, commercially available from Union Carbide Corp., Danbury, CT, and having the tradename IGEPAL, commercially available from Rhone- Poulenc Inc., Cranbury, N.J.

Examples of useful anionic non-fluorinated surfactants include dialkyl sulfosuccinates, having the tradename AEROSOL OT, commercially available from Cytec Industries, West Paterson, N.J.; alkyl sulfonates; alkyl aryl sulfonates; alkyl sulfates; alkyl ether sulfates; alkyl aryl ether sulfates; alkyl phosphates; and long-chain carboxylates.

Examples of useful cationic non-fluorinated surfactants include tetraalkylphosphonium halides and alkyltrimethylammonium halides, having the tradename ARQUAD, and the ethoxylated quaternary ammonium halides, having the tradename ETHOQUAD, both commercially available from Akzo Nobel Chemicals, Chicago, Ill.

Examples of useful amphoteric non-fluorinated surfactants include alkyldimethyl amine oxides, alkylcarboxamidoalkylenedimethyl amine oxides, aminopropionates, sulfobetaines, alkyl betaines, alkylamidobetaines, dihydroxyethyl glycinates, imidazoline acetates, imidazoline propionates, and imidazoline sulfonates.

c) Catanionic

A catanionic surfactant is a product prepared by either the neutralization reaction of an organic acid and an organic base or the reaction of a cationic or an amine oxide surfactant with an anionic surfactant in an aqueous solvent. It is generally preferred to prepare a catanionic surfactant by the acid-base method since this method does not produce a byproduct electrolyte. The resulting catanionic surfactant has two hydrophobes, making it generally more surface active than either of its two components individually. The hydrophobes may be saturated or unsaturated and fluorinated or non-fluorinated or a combination thereof. Preferably, one hydrophobe is fluorinated and the other is non-fluorinated.

A typical synthesis for a catanionic surfactant would be the reaction of an equi-normal mixture of an organic base or a cationic surfactant with an organic acid or an anionic surfactant in water. Typically, the larger the hydrophobes, the less soluble the catanionic surfactant is in water, and a cosolvent (for example, an alcohol) may be required to maintain a stock solution. Additionally, if a catanionic surfactant is to be used in a microemulsion of the invention, the catanionic surfactant may be prepared in situ, thereby possibly foregoing the addition of a cosolvent.

Typical catanionic surfactants useful in the microemulsions of the invention may be prepared from the reaction of perfluorocarboxylic or perfluorosulfonic acids with tetraalkylammonium hydroxides. Many of the useful tetraalkylammonium hydroxides are commercially available from Aldrich Chemical Co., Milwaukee Wis., as aqueous solutions. Many perfluorinated acids are also commercially available from Aldrich Chemical Co. as well as Minnesota Mining and Manufacturing Company or E.I. DuPont de Nemours and Co. Additionally, useful catanionic surfactants may be prepared from the reaction of hydrocarbon acids and tetrakis(polyfluoroalkyl)ammonium hydroxides.

Useful catanionic surfactants may also be prepared from the reaction of fluorinated cationic surfactants with hydrocarbon anionic surfactants or the reaction of fluorinated anionic surfactants with hydrocarbon cationic surfactants. Useful fluorinated cationic and anionic surfactants include those having the tradenames FLUORAD and ZONYL, commercially available from Minnesota Mining and Manufacturing Company and E.I. DuPont de Nemours and Co., respectively.

A particularly useful catanionic surfactant is tetrabutylammonium perfluorooctanoate made from the reaction of perfluorooctanoic acid and tetrabutyl ammonium hydroxide, with a cosolvent, for example, isopropanol, to maintain a homogeneous solution.

Generally, surfactant is present in the microemulsions of the invention at levels ranging from about 5 to about 30 percent by weight, preferably about 5 to about 20 percent by weight, and more preferably, about 5 to about 15 weight percent of the micro emulsion.

Cosolvents

The microemulsions of the invention may include one or more cosolvents. A "cosolvent" is a liquid having at least partial miscibility with HFE and/or water in the composition. Cosolvents may be added to the microemulsions of the invention to broaden the range of microemulsions that can be formed in mixtures of water, surfactants, and HFEs.

In general, useful cosolvents include alcohols, ethers, esters, ketones, hydrochlorocarbons, hydrochlorofluorocarbons, and hydrofluorocarbons. Preferably, the cosolvent is selected from the group consisting of alcohols, hydrochlorofluorocarbons, hydrochlorocarbons, and hydrofluorocarbons.

Representative examples of cosolvents which can be used in the microemulsions of the invention include methanol, ethanol, isopropanol, t-butyl alcohol, trans-1,2-dichloroethylene, methyl decanoate, t-butyl acetate, ethyl acetate, diethyl phthalate, 2-butanone, methyl isobutyl ketone, p-chlorobenzotrifluoride, trifluorotoluene, methylene chloride, chlorocyclohexane, 1-chlorobutane, 1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, and 1-hydropentadecafluoroheptane.

Cosolvents may generally be used in the microemulsions of the invention at levels of up to about 20 percent by weight of the water or HFE, whichever is present in greater amount.

The microemulsions of the invention may contain other additives such as electrolytes, acids, bases, inorganic compounds, organic compounds (for example, biocides, pharmaceutical agents), polymers, siloxane surfactants, polymeric surfactants, and the like, in either the oil or the aqueous phase.

Method of Making

In general, the microemulsions of the invention are made by simply mixing the components together. Some energy input in the form of, for instance, mild agitation may be required to accelerate microemulsion formation in some compositions. Once the microemulsion has formed, agitation would only be required to restore the microemulsion if the storage conditions had been changed and then re-established. The microemulsions of the invention are typically stable indefinitely under static storage conditions.

In choosing the components of the microemulsions of the invention, some general guidelines apply. Generally, the surfactants selected should be more soluble in the continuous phase than in the dispersed phase (Bancroft's Rule, Langmuir 1996, 12, 6351), although this is somewhat dependent on the temperature of the system and the water/oil ratio. For example, a surfactant can change its solubility from the continuous phase to the dispersed phase by changing the temperature, electrolyte concentration, or water/oil ratio of the microemulsion.

If the primary surfactant is a fluorinated nonionic surfactant, then a cosurfactant may be cationic, nonionic, catanionic, zwitterionic, or combinations thereof. The cosurfactant may be fluorinated or hydrogenated or both. If the primary surfactant is a fluorinated ionic surfactant, then a cosurfactant may be nonionic and fluorinated or non-fluorinated (hydrogenated).

When a catanionic surfactant containing one fluorinated hydrophobe and one non-fluorinated hydrophobe is used, the microemulsions of the invention form at lower temperatures the higher the fluorine content of the catanionic surfactant, when the amounts of HFE, water, and cosolvent (if present) are held constant. Conversely, the microemulsions of the invention tend to form at higher temperatures the higher the hydrocarbon content of the catanionic surfactant, all else held constant.

The microemulsions of the invention will now be illustrated in, but not limited by, the following examples.

EXAMPLES

All numerical levels are in weight percent unless otherwise indicated. Unless otherwise indicated, all ingredients are commercially available from Aldrich Chemical Co.

GLOSSARY 402 perfluorobutyl ethyl ether, commercially available from Minnesota Mining and Manufacturing Company 401 perfluorobutyl methyl ether, commercially available from Minnesota Mining and Manufacturing Company Water deionized and filtered water, having the tradename Millipore, 18 MOhms TBAPFO tetrabutylammonium perfluorooctanoate surfactant, made by reacting 11.02 g perfluorooctanoic acid with 16.39 g tetrabutylammonium hydroxide (using a 40 weight percent aqueous solution) with stirring. Isopropanol (9.76 g) was added to produce a single-phased solution. The resulting solution contained by weight 46.9 percent TBAPFO, 26.3 percent IPA, and 26.8 percent water TPrAPFO tetrapropylammonium perfluorooctanoate surfactant, made in situ by reacting equimolar amounts of tetrapropylammonium hydroxide and perfluorooctanoic acid DBDPrAPFO dibutyldipropylammonium perfluorooctanoate surfactant, made in situ by reacting equimolar amounts of perfluorooctanoic acid with tetrabutylammonium hydroxide/tetrapropylammonium hydroxide (1/1)

15-S-5 ethoxylated alcohol (nonionic hydrocarbon surfactant), commercially available from Union Carbide Corp, Danbury, Conn., having the tradename TERGITOL 15-S-5

MPEG-HFP an addition product of hexafluoropropylene trimer and poly(ethylene glycol) monomethyl ether (mw =350), prepared using methods described in U.S. Pat. No. 4,272,615, incorporated by reference herein OT-100 (bis(2-ethylhexyl)sulfosuccinate sodium salt), commercially available from Cytec Industries, having the tradename AEROSOL OT-100

FC-171 fluorinated alkyl alkoxylate (nonionic fluorinated surfactant), commercially available from Minnesota Mining and Manufacturing Company FC-143 ammonium perfluoroalkyl carboxylates (anionic fluorinated surfactant), commercially available from Minnesota Mining and Manufacturing Company FC-135 fluorinated alkyl quaternary ammonium iodides, (fluorinated cationic surfactant), commercially available from Minnesota Mining and Manufacturing Company FC-95 potassium perfluoroalkyl sulfonates, (anionic fluorinated surfactant), commercially available from Minnesota Mining and Manufacturing Company IPA isopropanol cosolvent Table 1 shows the compositions of Examples 1–19 and Comparative Example 1.

TABLE 1

| Component | 402 (HFE) (wt %) (g) | 401 (HFE) (wt. %) (g) | Water (wt %) (g) | TBAPFO (wt %) (g) | DBDPr APFO (wt %) (g) | TPrAPFO (wt %) (g) | FC 171 (wt %) (g) | FC-143 (wt %) (g) |
|---|---|---|---|---|---|---|---|---|
| Ex. 1 | 30.4 (1.0) | | 30.4 (1.0) | 15.2 (0.5) | | | 15.2 (0.5) | |
| Ex. 2 | 43.1 (4.04) | | 43.1 (4.04) | 5.35 (0.5) | | | 5.35 (0.5) | |
| Ex. 3 | 8.6 (0.21) | | 26.3 (1.0) | 41.2 (1.0) | | | | |
| Ex. 4 | 11.8 (0.31) | | 24.3 (0.64) | 38.0 (1.0) | | | 3.8 (0.1) | |
| Ex. 5 | 41.1 (3.0) | | 41.1 (3.0) | 6.9 (0.5) | | | 6.9 (0.5) | |
| Ex. 6 | 36.2 (3.0) | | 48.2 (4.0) | 6.0 (0.5) | | | 6.0 (0.5) | |
| Ex. 7 | 47.0 (3.8) | | 37.1 (3.0) | 6.2 (0.5) | | | 6.2 (0.5) | |
| Ex. 8 | 48.25 (4.0) | | 36.2 (3.0) | 6.0 (0.5) | | | 6.0 (0.5) | |
| Comp. Ex. 1 | 45.45 (5.0) | | 9.1 (1.0) | | | | | |
| Ex. 9 | 4.7 (3.0) | | 93.3 (60) | 0.8 (0.5) | | | 0.8 (0.5) | |
| Ex. 10 | 84.8 (9.0) | | 3.0 (0.21) | 4.7 (0.5) | | | 4.7 (0.5) | |
| Ex. 11 | | 73.3 (3600) | 8.4 (414) | | 9.15 (450) | | 9.15 (450) | |
| Ex. 12 | | 70.2 (3600) | 12.3 (630) | | | 8.75 (450) | 8.75 (450) | |
| Ex. 13 | | 14.3 (0.5) | 71.4 (2.5) | | | | 7.1 (0.25) | 7.1 (0.25) |
| Ex. 14 | 89.3 (5.0) | | 1.8 (0.1) | | | | 7.1 (0.4) | |
| Ex. 15 | 71.4 (5.0) | | 7.1 (0.5) | | | | 14.3 (1.0) | |
| Ex. 16 | 80.6 (5.0) | | 1.6 (0.1) | | | | 16.1 (1.0) | |
| Ex. 17 | 80.6 (5.0) | | 1.6 (0.1) | | | | 16.1 (1.0) | |
| Ex. 18 | 96.9 (5.0) | | 1.2 (0.06) | | | | | |

TABLE 1-continued

| Component | FC-95 (wt %) (g) | FC-135 (wt %) (g) | OT-100 (wt %) (g) | 15S5 (wt %) (g) | MPEG-HFP (wt. %) (g) | Total Surfactant (wt %) (g) | IPA (wt %) (g) |
|---|---|---|---|---|---|---|---|
| Ex. 19 | | | | | 54.0 (0.57) | 5.7 (0.06) | |
| Ex. 1 | | | | | | 30.4 (1.0) | 8.8 (0.29) |
| Ex. 2 | | | | | | 10.7 (1.0) | 3.1 (0.64) |
| Ex. 3 | | | | | | 41.2 (1.0) | 23.9 (0.58) |
| Ex. 4 | | | | | | 41.8 (1.1) | 22.1 (0.58) |
| Ex. 5 | | | | | | 13.8 (1.0) | 4.0 (0.29) |
| Ex. 6 | | | | | | 12.0 (0.5) | 3.5 (0.29) |
| Ex. 7 | | | | | | 12.4 (1.0) | 3.6 (0.29) |
| Ex. 8 | | | | | | 12.0 (1.0) | 3.5 (0.29) |
| Comp. Ex. 1 | | | | | | | 45.45 (5.0) |
| Ex. 9 | | | | | | 1.6 (1.0) | 0.5 (0.29) |
| Ex. 10 | | | | | | 9.4 (1.0) | 2.7 (0.29) |
| Ex. 11 | | | | | | 18.3 (900) | |
| Ex. 12 | | | | | | 17.5 (900) | |
| Ex. 13 | | | | | | 14.2 (0.5) | |
| Ex. 14 | 1.8 (0.1) | | | | | 8.9 (0.5) | |
| Ex. 15 | 7.1 (0.5) | | | | | 21.4 (1.5) | |
| Ex. 16 | | | 1.6 (0.1) | | | 21.6 (1.1) | |
| Ex. 17 | | | | 1.6 (0.1) | | 21.6 (1.1) | |
| Ex. 18 | | | | | 1.9 (0.1) | 1.9 (0.1) | |
| Ex. 19 | | 15.2 (0.16) | 9.5 (0.1) | | | 24.7 (0.26) | 15.2 (0.16) |

Example 1

The surfactants were combined. HFE 402 was added to this mixture and was stirred to form a single-phased, yellowish, transparent solution. The water was added and the mixture was stirred at room temperature (about 24° C.) to form a microemulsion.

Example 2

Additional water and HFE 402 was added (incrementally, with mixing) to the microemulsion of Example 1 before to phase separation occurred. Just prior to phase separation, the microemulsion had the formulation shown in Table 1. Further addition of water (0.1 g) and HFE 402 (0.1 g) to the microemulsion resulted in phase separation at room temperature. Upon heating the separated mixture to slightly above room temperature (about 50° C.), it re-formed a microemulsion.

Example 3

HFE 402 was added incrementally to a solution containing TBAPFO, water, and isopropanol until a phase separation occurred. Just prior to phase separation, the composition shown in Table 1 formed a microemulsion. After formation of the microemulsion 4.1 weight percent HFE 402 (0.1 g) was added causing phase separation. The phase separated composition formed a microemulsion upon cooling to a temperature of about 5° C. This example in combination with Example 1 shows that inclusion of a fluorinated nonionic surfactant allows a broader range of microemulsions to be obtained.

Example 4

The composition of Example 3 was warmed to room temperature and the phases separated. FC 171 (0.1 g) was added to the separated composition to form a microemulsion. The composition of this microemulsion is shown in Table 1. An additional (0.1 g) HFE 402 was added to this composition and the phases separated. The separated solution formed a microemulsion upon cooling to a temperature of about 5° C. This example shows that the amounts of water and hydrofluoroether in a microemulsion can be increased with the addition of a fluorinated nonionic surfactant to the composition.

Comparative Example 1

Equal weights of HFE 402 and isopropanol were combined to form a solution. Water was added to this solution until phase separation occurred. The composition of the mixture formed just prior to phase separation is shown in Table 1. This example shows that equal amounts of IPA and a hydrofluoroether could only solubilize about 9 weight percent water.

Example 5

The components were mixed together and the composition formed a nearly transparent microemulsion at room temperature.

Example 6

An additional (1.0 g) water was added to the microemulsion of Example 5 at room temperature. The composition remained a microemulsion at room temperature.

Example 7

The components were mixed together and the composition formed a nearly transparent microemulsion that did not separate at room temperature.

Example 8

An additional (0.2 g) HFE 402 was added to the microemulsion of Example 7. After 60 minutes, phase separation was noted. The separated composition would form a microemulsion upon heating to about 35° C.

Example 9

The components were mixed together and the composition formed a microemulsion at room temperature.

Example 10

The components were mixed together and the composition formed a microemulsion at room temperature.

Example 11

The components were mixed together and the composition formed a microemulsion at room temperature. This composition demonstrates a microemulsion without a cosolvent.

Example 12

The components were mixed together and the composition formed a microemulsion at the boiling point of HFE 401 (60° C.). This composition was a two-phase system at room temperature.

Example 13

The components were mixed together and the composition formed a microemulsion that was maintained from room temperature up to the boiling point of HFE 401 (60° C.).

Example 14

HFE 402 and surfactant components were mixed together and the composition formed a transparent, yellow solution. Water was added until phase separation. The composition of the microemulsion just prior to phase separation is shown in Table 1.

Example 15

FC-95 and HFE 402 were combined. FC-171 was added until a transparent solution was obtained. Water was added until phase separation occurred. Table 1 shows the composition of the microemulsion just prior to phase separation.

Example 16

The surfactants and HFE 402 were mixed resulting in a brown transparent solution. Water was added slowly until phase separation occurred. Table 1 shows the composition of the microemulsion just prior to phase separation.

Example 17

The surfactants were mixed with HFE 402. Water was slowly added and resulted in a microemulsion upon shaking. Table 1 shows the composition of the microemulsion.

Example 18

The surfactant and HFE 402 were mixed and formed a birefringent solution. The addition of water produced a slightly hazy microemulsion.

Example 19

The surfactant and HFE 402 were mixed until the surfactant dissolved. Water was added until phase separation. Table 1 shows the composition of the microemulsion just prior to phase separation.

The examples show that relatively large amounts of water and HFEs may be combined to produce microemulsions.

Comparative Example 2

Water was added to an 80/20 HFE 401/ethanol solution until phase separation. The solution could only solubilize less than 5 weight percent water just prior to separating. The final composition just prior to separation was 76 weight percent (4 g) HFE 401, 19 weight percent (1 g) ethanol, and 4.8 weight percent (0.25 g) water.

Comparative Example 3

HFE 401 was added to an 80/20 water/ethanol solution until phase separation. The solution could only solubilize about 2 weight percent HFE 401 just prior to separating. The final composition was 78.4 weight percent (4 g) water, 19.6 weight percent (1 g) ethanol, and 2 weight percent (0.1 g) HFE 401.

Comparative Example 4

Water was added to a 50/50 HFE 401/ethanol solution until phase separation. The solution separated upon addition of 7.7 weight percent (0.33 g) water. The final composition was 46.15 weight percent each of (5 g) HFE 401, and (5 g) ethanol, and 7.7 weight percent (0.5) water.

Comparative Example 5

A 50/50 HFE 401/water mixture required (in the final solution) 65.2 weight percent of ethanol to form a one-phase mixture. Then final composition was 17.4 weight percent each of (1 g) HFE 401, and (1 g) water, and 65.2 weight percent (3.75 g) ethanol.

Comparative Examples 2–5 show that ethanol is a poor surfactant for HFE/water microemulsions.

What is claimed is:

1. A composition comprising:
   a) from 0.1 to 99 parts by weight hydrofluoroether;
   b) from 99.9 to 1 weight percent of water, the sum of a) and b) equaling 100 parts; and c) fluorinated surfactant, wherein said composition comprises a microemulsion, and wherein said hydrofluoroether comprises at least one: mono-, di, or trialkoxy-substituted perfluoroalkane perfluorocycloalkane, perfluorocycloalkyl-containing perfluoroalkane, or perfluorocycloalkylene-containing perfluoroalkane compound or compound having the formula: H—R$_f$'-(O—R$_f$")$_y$—O—R"—H, wherein: R$_f$' is a divalent perfluorinated organic radical having from 1 to about 12 carbon atoms; R$_f$" is a divalent perfluorinated organic radical having from 1 to about 6 carbon atoms, R" is a divalent organic radical having from 1 to 6 carbon atoms; and y is an integer from 0 to 4.

2. The composition of claim 1, further comprising a cosolvent.

3. The composition of claim 1, wherein the composition is a microemulsion between the temperatures of −10° C. and the boiling point temperature of said hydrofluoroether or water, whichever is lower.

4. The composition of claim 1, further comprising a cosurfactant.

5. The composition of claim 1 wherein said hydrofluoroether is selected from the group consisting of HC$_3$F$_6$OC$_3$F$_6$H; HC$_3$F$_6$OCH$_3$; HCF$_2$O(C$_2$F$_4$O)$_n$(CF$_2$O)$_m$CF$_2$H, wherein m=0 to 2 and n=0 to 3; HCF$_2$CF$_2$OCF$_2$C(CF$_3$)$_2$CF$_2$OC$_2$F$_4$H; and combinations thereof.

6. The composition of claim 1, wherein the fluorinated surfactant is present in the composition at a level of from about 5 to about 30 weight percent of the total composition.

7. The composition of claim 1, wherein the composition is a microemulsion between the temperatures of 0° C. and the boiling point temperature of said hydrofluoroether or water, whichever is lower.

8. The composition of claim 1, wherein the fluorinated surfactant is nonionic.

9. The composition of claim 1, wherein the fluorinated surfactant has a fluorinated aliphatic group containing at least 3 and no more than about 20 carbon atoms.

10. The composition of claim 1, wherein the fluorinated surfactant has a polar hydrophilic group selected from the group consisting of carboxylate, sulfonate, sulfate, ether sulfate, phosphate, quaternary ammonium, protonated ammonium, sulfonium, phosphonium, polyoxyethylene, polyoxypropylene, betaine, sulfobetaine, aminocarboxyl, and amine oxide.

11. The composition of claim 10, wherein the polar hydrophilic group is a polyoxyethylene or polyoxypropylene group.

12. The composition of claim 2, wherein the cosolvent is selected from the group consisting of alcohols, ethers, esters, ketones, hydrochlorocarbons, hydrochlorofluorocarbons, hydrofluorocarbons, and mixtures thereof.

13. The composition of claim 2, wherein the cosolvent is present in the composition at a level of up to about 20 percent by weight of the water or of the hydrofluoroether, whichever is present in greater amount.

14. The composition of claim 4, wherein the cosurfactant is cationic, nonionic, catanionic, amphoteric, or combinations thereof.

15. The composition of claim 1, wherein the hydrofluoroether is C$_3$F$_7$OCH$_3$, C$_4$F$_9$OCH$_3$, C$_4$F$_9$OC$_2$H$_5$, n-C$_3$F$_7$OCH$_3$, (CF$_3$)$_2$CFOCH$_3$, n-C$_4$F$_9$OCH$_3$, (CF$_3$)$_2$CFCF$_2$OCH$_3$, n-C$_4$F$_9$OC$_2$H$_5$, (CF$_3$)$_2$CFCF$_2$OC$_2$H$_5$, (C$_3$F$_7$)$_3$COCH$_3$, CH$_3$O(CF$_2$)$_4$OCH$_3$, CH$_3$O(CF$_2$)$_6$OCH$_3$, c-C$_6$F$_{11}$CF$_2$OCH$_3$, or combinations thereof.

16. The composition of claim 15, wherein the fluorinated surfactant is nonionic.

17. The composition of claim 16, further comprising a cosolvent.

18. The composition of claim 17, wherein the cosolvent is an alcohol.

19. The composition of claim 18, further comprising a cosurfactant.

20. The composition of claim 19, wherein the cosurfactant is catanionic.

21. A composition comprising:
a) from 0.1 to 99 parts by weight hydrofluoroether;
b) from 99.9 to 1 weight percent of water, the sum of a) and b) equaling 100 parts; and
c) fluorinated surfactant, wherein said composition comprises a microemulsion, and wherein said hydrofluoroether has the formula $$R_f\text{-}(O\text{—}R_h)_x$$

wherein:

x is from 1 to about 3;

when x is 1, R$_f$ is selected from the group consisting of linear or branched perfluoroalkyl groups having from 2 to about 15 carbons, perfluorocycloalkyl groups having from 3 to about 12 carbon atoms, and perfluorocycloalkyl-containing perfluoroalkyl groups having from 5 to about 15 carbon atoms;

when x is 2, R$_f$ is selected from the group consisting of linear or branched perfluoroalkanediyl groups or perfluoroalkylidene groups having from 2 to about 15 carbon atoms, perfluorocycloalkyl- or perfluorocycloalkylene-containing perfluoroalkanediyl or perfluoroalkylidene groups having from 6 to about 15 carbon atoms, and perfluorocycloalkylidene groups having from 3 to about 12 carbon atoms;

when x is 3, R$_f$ is selected from the group consisting of linear or branched perfluoroalkanetriyl groups or perfluoroalkylidene groups having from 2 to about 15 carbon atoms, perfluorocycloalkyl- or perfluorocycloalkylene-containing perfluoroalkanetriyl or perfluoroalkylidene groups, having from 6 to about 15 carbon atoms, and perfluorocycloalkanetriyl groups having from 3 to about 12 carbon atoms;

in all cases, R$_f$ can be optionally terminated with an F$_5$S- group;

each R$_h$ is independently selected from the group consisting of linear or branched alkyl groups having from 1 to about 8 carbon atoms, cycloalkyl-containing alkyl groups having from 4 to about 8 carbon atoms, and cycloalkyl groups having from 3 to about 8 carbon atoms;

wherein either or both of the groups R$_f$ and R$_h$ can optionally contain one or more catenary heteroatoms; and wherein the sum of the number of carbon atoms in the R$_f$ group and the number of carbon atoms in the R$_h$ group(s) is greater or equal to 4.

* * * * *

UNITED STATES PATENT AND TRADEMARK OFFICE
CERTIFICATE OF CORRECTION

PATENT NO. : 6,127,430
DATED : October 3, 2000
INVENTOR(S) : Baran, Jr. et al.

It is certified that error appears in the above-identified patent and that said Letters Patent is hereby corrected as shown below:

Column 1,
Line 2, delete "HYDROFLUROETHERS" and insert in place thereof
-- HYDROFLUOROETHERS --.

Column 3,
Line 48, delete "perfluoroalkanedlyl" and insert in place thereof
-- perfluoroalkanediyl --.

Column 8,
Line 35, delete "ZEORORAF" and insert in place thereof -- ZEORORAH --.

Column 9,
Line 33, delete "$CH_2COO^{-K+}$" and insert in place thereof -- $CH_2COO^-K^+$ --.
Line 39, delete "$C_7F_{15}CF(CF_3)SO_2N(H)C_3H_6N^+(CH_3)_2O^{+}$" and insert in place thereof
-- $C_7F_{15}CF(CF_3)SO_2N(H)C_3H_6N^+(CH_3)_2O^-$ --.
Line 49, delete "$C_6F_{13}SO_2N(C_2H_4COO^{-)C}{}_3H_6N^+(CH_3)_2H$" and insert in place thereof
-- $C_6F_{13}SO_2N(C_2H_4COO^-)C_3H_6N^+(CH_3)_2H$ --.
Line 51, delete "$C_6F_{13}SO_2N(C_3H_6SO_3^{-)c}{}_3H_6N^+(CH_3)_2C_2H_4OH$" and insert in place
thereof -- $C_6F_{13}SO_2N(C_3H_6SO_3^-)C_3H_6N^+(CH_3)_2C_2H_4OH$ --.
Line 52, delete "$C_6F_{13}SO_2N(CH_2CHOHCH_2SO_3^3)C_3H_6N^+(CH_3)_2C_2H_4OH$" and insert
in place thereof -- $C_6F_{13}SO_2N(CH_2CHOHCH_2SO_3)C_3H_6N^+(CH_3)_2C_2H_4OH$ --.
Line 58, delete "$C_6F_{13}SO_2N(C_2H_5)C_3H_6N(H)CH_2CH(OH)CH_2SO_3^{-Na+}$" and insert in
place thereof -- $C_6F_{13}SO_2N(C_2H_5)C_3H_6N(H)CH_2CH(OH)CH_2SO_3^-Na^+$ --.

Column 12,
Line 17, delete "1-dichloro-1-fluoroethane" and insert in place thereof -- 1,1-dichloro-1-
fluoroethane --.

UNITED STATES PATENT AND TRADEMARK OFFICE
CERTIFICATE OF CORRECTION

PATENT NO.   : 6,127,430
DATED        : October 3, 2000
INVENTOR(S)  : Baran, Jr. et al.

It is certified that error appears in the above-identified patent and that said Letters Patent is hereby corrected as shown below:

Column 19,
Lines 63 and 64, delete "$(C_3)_3COCH_3$," and insert in place thereof -- $(CF_3)_3COCH_3$, --.

Signed and Sealed this

Twenty-seventh Day of August, 2002

Attest:

JAMES E. ROGAN
Attesting Officer     Director of the United States Patent and Trademark Office